(12) United States Patent
Koch et al.

(10) Patent No.: US 10,884,091 B2
(45) Date of Patent: Jan. 5, 2021

(54) VOXELWISE SPECTRAL PROFILE MODELING FOR USE IN MULTISPECTRAL MAGNETIC RESONANCE IMAGING

(71) Applicant: THE MEDICAL COLLEGE OF WISCONSIN, INC., Milwaukee, WI (US)

(72) Inventors: Kevin M. Koch, Wauwatosa, WI (US); Suryanarayanan Kaushik, Milwaukee, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 0 days.

(21) Appl. No.: 16/098,659

(22) PCT Filed: May 5, 2017

(86) PCT No.: PCT/US2017/031226
§ 371 (c)(1),
(2) Date: Nov. 2, 2018

(87) PCT Pub. No.: WO2017/192952
PCT Pub. Date: Nov. 9, 2017

(65) Prior Publication Data
US 2019/0146049 A1 May 16, 2019

Related U.S. Application Data

(60) Provisional application No. 62/332,104, filed on May 5, 2016, provisional application No. 62/482,796, filed on Apr. 7, 2017.

(51) Int. Cl.
*G01R 33/565* (2006.01)
*G01R 33/56* (2006.01)
(Continued)

(52) U.S. Cl.
CPC ..... *G01R 33/56536* (2013.01); *G01R 33/243* (2013.01); *G01R 33/5607* (2013.01); *A61B 5/055* (2013.01); *G01R 33/58* (2013.01)

(58) Field of Classification Search
None
See application file for complete search history.

(56) References Cited

U.S. PATENT DOCUMENTS 6,208,138 B1 * 3/2001 Lai ..................... G01R 33/3875
                                                            324/307
6,750,651 B2    6/2004 Overall
(Continued)

FOREIGN PATENT DOCUMENTS

| WO | 2003100465 A1 | 12/2003 |
| WO | 2012123830 A1 | 9/2012 |

(Continued)

OTHER PUBLICATIONS

Thevenaz et al. Image Interpolation and Re sampling, 2000, Handbook of medical Imaging, Processing and Analysis, pp. 393-420 (Year: 2000).*

(Continued)

*Primary Examiner* — Jermele M Hollington
(74) *Attorney, Agent, or Firm* — Quarles & Brady LLP

(57) ABSTRACT

Described here are systems and methods for using a magnetic resonance imaging ("MRI") system to estimate parameters of spectral profiles contained in multispectral data acquired using multispectral imaging ("MSI") techniques, such as MAVRIC. These spectral profile parameters are reliably extracted using an iterative perturbation theory technique and utilized in a number of different applications, including fat suppression, artifact correction, and providing accelerated data acquisitions.

19 Claims, 8 Drawing Sheets

(51) Int. Cl.
  *G01R 33/24* (2006.01)
  *G01R 33/58* (2006.01)
  *A61B 5/055* (2006.01)

(56) References Cited

U.S. PATENT DOCUMENTS

| | | | | |
|---|---|---|---|---|
| 7,116,749 | B2 * | 10/2006 | Besson | A61B 6/032 378/16 |
| 7,535,227 | B1 | 5/2009 | Koch | |
| 7,821,264 | B2 | 10/2010 | Koch | |
| 7,928,729 | B2 | 4/2011 | Hargreaves | |
| 7,952,356 | B2 | 5/2011 | Koch | |
| 8,421,459 | B2 | 4/2013 | Koch | |
| 8,482,279 | B2 | 7/2013 | Chen | |
| 8,749,236 | B2 | 6/2014 | Miyazaki | |
| 9,018,951 | B2 * | 4/2015 | Lai | G01R 33/56563 324/307 |
| 10,101,424 | B2 * | 10/2018 | Levine | G01R 33/4835 |
| 10,712,418 | B2 * | 7/2020 | Koch | G01R 33/4824 |
| 10,718,838 | B2 * | 7/2020 | Koch | A61B 5/055 |
| 2005/0220265 | A1 * | 10/2005 | Besson | A61B 6/488 378/16 |
| 2010/0308828 | A1 * | 12/2010 | Koch | G01R 33/243 324/312 |
| 2012/0176131 | A1 * | 7/2012 | Madhuranthakam | G01R 33/4828 324/307 |
| 2012/0262167 | A1 * | 10/2012 | Lai | G01R 33/5611 324/309 |
| 2013/0076356 | A1 | 3/2013 | Jellus | |
| 2013/0265046 | A1 | 10/2013 | Koch | |
| 2013/0278254 | A1 * | 10/2013 | Reeder | G01R 33/485 324/307 |
| 2014/0002080 | A1 | 1/2014 | Harder | |
| 2014/0121492 | A1 * | 5/2014 | Boernert | G01R 33/4828 600/410 |
| 2014/0361776 | A1 * | 12/2014 | Miyazaki | G01R 33/5605 324/322 |
| 2015/0346304 | A1 * | 12/2015 | Hu | A61B 5/055 600/411 |
| 2016/0154080 | A1 * | 6/2016 | Wiens | G01R 33/56536 324/309 |
| 2018/0136297 | A1 | 5/2018 | Koch | |
| 2018/0172788 | A1 * | 6/2018 | Levine | G01R 33/4835 |
| 2018/0292491 | A1 | 10/2018 | Koch | |

FOREIGN PATENT DOCUMENTS

| | | |
|---|---|---|
| WO | 2014115043 A1 | 7/2014 |
| WO | 2016187014 A1 | 11/2016 |

OTHER PUBLICATIONS

Then, Ca et al. New MR imaging methods for metallic implants in the knee: Artifact correction and clinical impact. Journal of Magnetic Resonance Imaging, 33(5):1121-1127, Apr. 2011.
FDA. Metal-on-Metal Hip Implants: FDA Safety Communication. http://www.fda.gov/MedicalDevices/Safety/AlertsandNOtices/ucm335775.htm. Issued Jan. 17,2013. Accessed: Oct. 8, 2014.
Fritz, J, et al. "MR imaging of hip arthroplasty implants." Radiographics 34.4 (2014): E106-E132.
GE Healthcare. Mavric SL—commercial site. Pulished Jul. 22, 2013. http://wwwlgehealthcare.com/en/products/categories/magnetic_resonance_imaging/musculoskeletal_imaging/mavric_sl. Accessed: Sep. 15, 2015.
Hargreaves, BA et al. Fast 2D imaging for distortion correction near metal implants, Proc. ISMRM, 2014. #615.
Hargreaves, BA et al. Metal-Induced Artifacts in Mrl American Journal of Roentgenology, 197(3):547-555, Aug. 2011.
Hayter, CL et al. Imaging of metal-on-metal hip resurfacing. Orthopedic Clinics of North America, 42(2):195-205, 2011.
Hayter, CL et al. MRI After Arthroplasty: Comparison of Mavric and Conventional Fast Spin-Echo Techniques. American Journal of Roentgenology, 197(3):W405—W411, Sep. 2011.
Hayter, CL et al. MRI findings in painful metal-on-metal hip arthroplasty. American Journal of Roentgenology, 199 (4):884-893, 2012.
International Searching Authority. International Search Report and Written Opinion for application.
Kaushik, SS et al. External calibration of the spectral coverage for three-dimensional multispectral MRI. (2015); Magnetic Resonance in Medicine, published online: Nov. 24, 2015.
Kaushik, SS. ISMRM, Clinically Viable Diffusion-Weighted Imaging Near Metal using 2D-MSI Propeller Duo, Proc ISMRM 2016, #370.
Koch, KM et al. "Spectral-Model Based Undersampling of Multi-Phase MSI: Application to Diffusion-Weighted maging Near Metal." ISMRM 2017.
Koch, KM et al. A multispectral three—dimensional acquisition technique for imaging near metal implants. Magn Reson Med 2009;61:381-390.
Koch, KM et al. Imaging near metal with a MAVRICSEMAC hybrid. Magnetic Resonance in Medicine, 65:71-82, 2011.
Koch, KM et al. Imaging near metal: The impact of extreme static local field gradients on frequency encoding Processes. Magnetic Resonance in Medicine, 71(6):2024-2034, Jul. 2013.
Koch, KM et al. Magnetic resonance imaging near metal implants. J Magn Reson Imaging 32:773-87 (2010).
Koch, KM et al. Non-CPMG Multi-Spectral Propeller for Diffusion-Weighted Imaging Near Metal Implants, Proc SMRM, 2015, #101.
Koff, MF et al. Quantifying image distortion of orthopedic materials in magnetic resonance imaging. Journal of Magnetic Resonance Imaging, 38(3):610-618,2013.
Kurtz, S, et al. "Projections of primary and revision hip and knee arthroplasty in the United States from 2005 to 2030." JBJS 894 (2007): 780-785.
Lee, YH et al. Feasibility of Fat-saturated T2-weighted Magnetic Resonance Imaging with Slice Encoding for Metal Artifact Correction (SEMAC) at 3T. Magnetic Resonance Imaging, 2014.
Lee, YH et al. Usefulness of slice encoding for metal artifact correction (SEMAC) for reducing metallic artifacts in 3T MRI. Magnetic resonance imaging, 31(5):703-706, 2013.
Liebl, H et al. In vitro assessment of knee MRI in the presence of metal implants comparing MAVRIC-SL and conventional fast spin echo sequences at 1.5 and 3T field strength. Journal of Magnetic Resonance Imaging, 2014.
Lu, W et al. SEMAC: Slice encoding for metal artifact correction in MRI. Magnetic Resonance in Medicine, 62:66-76, 2009.
Moore EH. On the reciprocal of the general algebraic matrix. Bulletin of the American Mathematical Society, 26 :394-395):38, 1920.
Nawabi, DH et al. Magnetic resonance imaging findings in symptomatic versus asymptomatic subjects following metal-on-metal hip resurfacing arthroplasty. The Journal of Bone & Joint Surgery, 95(10):895-902, 2013.
Penrose R. A generalized inverse for matrices. In Proc. Cambridge Philos. Soc, vol. 51, pp. 406-413. Cambridge Univ Press, 1955.
Philips O-Mar—commercial site. http://www.philips.co.uk/healthcare/education-resourcesitechnologies/mri/scanwise-implant. Accessed: Jan. 12, 2016.
Pipe, J. G., et al. Multishot diffusion-weighted FSE using Propeller MRI. Magnetic Resonance in Medicine, 47(1), 2002,42-52.
Potter, HG et al. Magnetic resonance imaging after total hip arthroplasty: evaluation of periprosthetic soft tissue. J. Bone Joint Surg. Am., 86-A:1947-1954, 2004.
Shi, X, et al. "Metallic implant geometry and susceptibility estimation using multispectral B0 field maps." Magnetic resonance in medicine 77.6 (2017): 2402-2413.
Siemens Syngo Warp Metal Artifact Reduction (pdf). Published Feb. 2012. http://www.healthcare.siemens.com/siemens_hwem-hwem_ssxa_websites-context-root/wcm/idcisiemens_hwem-hwem_ssxa_websites-context-root/wcm/ dc/groups/publici©global/©imaging/

(56) References Cited

OTHER PUBLICATIONS

@mri/documents/download/ mdaw/mzixl-edispl syngo_warp_metal_ artifact_reduction_techniques_in_mri-00284426.pdf. Accessed: Aug. 5, 2020.

Smith, MR. et al. Accelerating sequences in the presence of metal by exploiting the spatial distribution of off-resonance. Magn Reson Med. Dec. 2014;72(6):1658-67.

Sutter, R et al. Reduction of metal artifacts in patients with total hip arthroplasty with slice-encoding metal artifact aorrection and view-angle tilting MR imaging. Radiology, 265(1):204-214, 2012.

Sutter, R et al. Total Knee Arthroplasty MRI Featuring Slice-Encoding for Metal Artifact Correction: Reduction of Artifacts for STIR and Proton Density-Weighted Sequences. American Journal of Roentgenology, 201(6):1315-1324, 2013.

Toms, AP et al. MRI of early symptomatic metal-on-metal total hip arthroplasty: a retrospective review of radiological Findings in 20 hips. Clinical Radiology, 63:49-58, 2008.

Weber, H., et al., MR thermometry near metallic devices using multispectral imaging. Magnetic Resonance in Medicine (Early View), 2016.

White, L. M., et al. "Complications of total hip arthroplasty: MR imaging—initial experience." Radiology 215.1 (2000): 254-262.

\* cited by examiner

RESONANCE FREQUENCY OFFSET

RESONANCE FREQUENCY OFFSET

VOXELWISE SPECTRAL PROFILE MODELING FOR USE IN MULTISPECTRAL MAGNETIC RESONANCE IMAGING

CROSS-REFERENCE TO RELATED APPLICATIONS

This application represents the national stage entry of PCT International Application No. PCT/US2017/031226 filed on May 5, 2017, which claims the benefit of U.S. Provisional Patent Application Ser. No. 62/332,104, filed on May 5, 2016 and entitled 'VOXELWISE SPRECTRAL PROFILING MODELING FOR USE IN MULTISPECTRAL MAGNETIC RESONANCE IMAGING," and claims the benefit of U.S. Provisional Patent Application Ser. No. 62/482,796, filed on Apr. 7, 2017, and entitled "VOXELWISE SPECTRAL PROFILE MODELING FOR USE IN MULTI SPECTRAL MAGNETIC RESONANCE IMAGING," both of which are herein incorporated by reference in their entirety.

BACKGROUND

Metallic device implantation is used to manage a wide variety of acute and chronic medical conditions. The need for diagnostic imaging in the presence of orthopedic implants is accentuated by accelerating installations of both primary and revised joint replacements.

Assessing bone and soft tissue in the vicinity of implanted orthopaedic devices is vital for identification of complications related to the implants themselves, such as the adverse local tissue reactions often found near total hip replacements. In addition, assessment of the region near implanted devices is required for the evaluation of pain following instrumentation, which may reflect a diverse set of conditions, including infection, osteonecrosis, and recurrent tumor.

Magnetic resonance imaging ("MRI") soft-tissue contrast adds substantial value when assessing the tissue envelope around metallic implants. Despite this inherent utility, magnetic susceptibility artifacts generated by implants have historically limited MRI's practical utility in assessments of instrumented joints. In response to this clinical need, three-dimensional multispectral imaging ("3D-MSI") technology was introduced to the MRI research community as an imaging technique that can reduce susceptibility artifacts caused by implanted devices.

Despite the initial success of 3D-MSI techniques in reducing susceptibility artifacts and enabling improved clinical assessments in the vicinity of metallic hardware, there are remaining challenged in 3D-MSI capabilities.

SUMMARY OF THE DISCLOSURE

The present disclosure addresses the aforementioned drawbacks by providing methods for using reliably estimated spectral profile information for accelerating multispectral imaging acquisitions, suppressing fat signals in multispectral magnetic resonance images, and removing pile-up intensity artifacts in multispectral magnetic resonance images.

Multispectral data are acquired from a subject with an MRI system using a multispectral imaging (MSI) acquisition is provided to a computer system. Spectral profile parameters are estimated at each voxel in the multispectral data, wherein the spectral profile parameters are based on modeling signals at each voxel using a spectral profile model. The spectral profile parameters may include an amplitude, center frequency, and width of the spectral profile at each voxel.

It is one aspect of the disclosure to provide methods for accelerating MSI acquisitions, in which spectral profile parameters can be estimated from calibration data. Undersampled multispectral data are then acquired from the subject and missing multispectral data are estimated using the estimated spectral profile parameters. An image of the subject can then be reconstructed from the undersampled multispectral data and the estimated missing multispectral data.

It is another aspect of the disclosure to provide methods for accelerating MSI acquisitions in which multispectral data acquired from a subject with an MRI system are provided to a computer system. The multispectral data contain at least some multispectral data that are undersampled in a spectral domain. Multispectral calibration data are also provided to the computer system, and a spectral model is generated based at least in part on the multispectral calibration data. Missing multispectral data that missing in the provided multispectral data are estimated using the spectral model. An image of the subject is then reconstructed from the provided multispectral data and the estimated missing multispectral data.

It is another aspect of the disclosure to provide methods for fat suppression, in which a chemical shift fraction associated with signal contributions from fat spins can be estimated from the estimated width of the spectral profile. An image of the subject that is reconstructed from the multispectral data can then be processed to suppress signal contributions from fat spins in the reconstructed image using the estimated chemical shift fraction.

It is another aspect of the disclosure to provide methods for pile-up intensity artifact reduction, in which the width of the spectral profile can be used to identify voxels that are associated with pile-up intensity artifacts. These voxels in the multispectral data can then be processed to remove the pile-up intensity artifacts. An image in which pile-up intensity artifacts are mitigated can then be reconstructed from the processed multispectral data.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and methods for using a magnetic resonance imaging ("MRI") system to estimate parameters of spectral profiles contained in multispectral data acquired using multispectral imaging ("MSI") techniques, such as MAVRIC. In most MSI techniques, the spectral profile information in the multispectral data is disregarded after spatial/spectral combination of the acquired images. It is a discovery of the present invention that, despite the relatively coarse spectral resolution and noisy spectral signature, this spectral information can be reliably extracted and utilized in a number of different applications.

As one specific, but non-limiting example, it is a discovery of the present invention that the estimated parameters of the spectral profiles contained in the multispectral data can be used to remove or otherwise suppress the signal contribution from fat spins in images acquired with MSI techniques. As a result, fat suppression can be achieved in MSI acquisitions without the need for preparation radio frequency ("RF") pulses or additional scans. Other example applications of the estimated spectral profile parameters are described below.

The magnetic susceptibility differences between metallic implants and surrounding bone and tissues range between hundreds and thousands of parts per million ("ppm"). Accordingly, the induced Larmor frequency offsets, $\delta v_0 = \gamma \delta B_0$, near implants approach 12-15 kHz at 1.5 T, and 24-30 kHz at 3 T.

In the presence of an induced off-resonance frequency distribution, $\delta v_0(r)$, the frequency-encoded dimension (e.g., the x-direction) in a spin-warp image follows the following bulk displacement relationship, $$\rho(r) \xrightarrow{\delta v_0(r)} \rho\left(x - \frac{2\pi \delta v_0(r)}{\gamma G_r}, y, z\right); \quad (1)$$

where $r=(x,y,z)$, and $G_r$, is the amplitude of the applied frequency-encoding gradient. Stepped phase-encoding dimensions in a spin-warp image are not susceptible to distortions from off-resonance effects. For notational simplicity, logical (x,y,z) coordinates can be used to represent the readout/frequency-encode, phase-encode, and slice-encode/phase-encode directions, respectively.

In MSI data acquisitions, heavily overlapping Gaussian spectral bin profiles are typically used. These overlapping Gaussian spectral windows, $G_b(V)$, are constructed such that, $$\sum_{b=1}^{N_b} G_b(v) \approx 1 \forall v; \quad (2)$$

where b is the spectral bin index and V is the frequency offset. This condition ensures that a homogeneous response is maintained when the spectral bins are combined to form the composite image.

Figure 1:
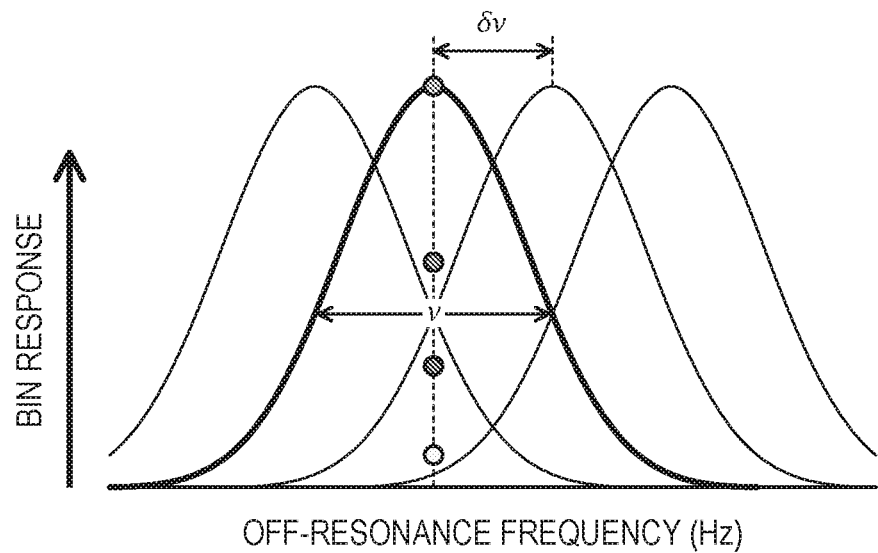
FIG. 1 shows multiple overlapping Gaussian spectral bins used for exciting a single spin isochromat in multispectral imaging.
Figure 2:
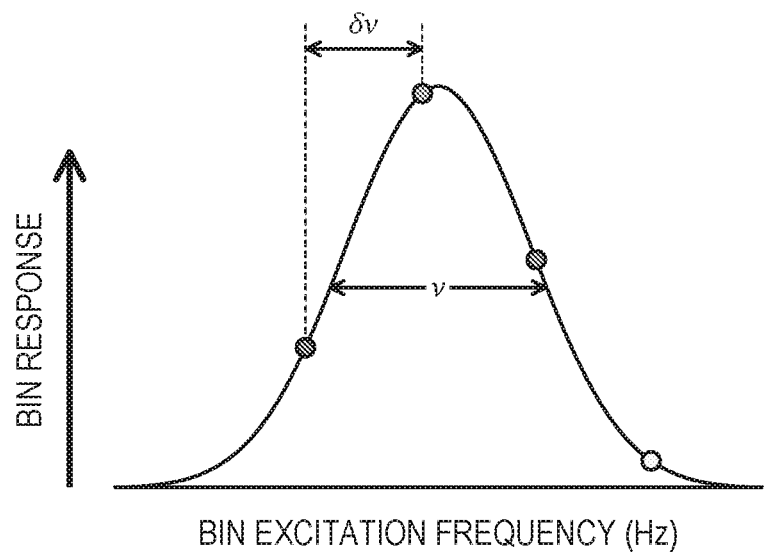
FIG. 2 shows a transformation along the x-axis of FIG. 1 to convert spin isochromat precessional frequency to central bin excitation frequency (i.e., the frequency offset of each bin excitation).

Consider a set of spectral bins in the spectral domain, $$f(v_{bin})|_{x,y,z} = I_b(x,y,z,v_{bin}) \quad (3);$$

where $v_{bin}$ is the central frequency-offset of a given spectral bin. Typically, a conventional MSI (e.g., a MAVRIC) dataset will provide 3-5 spectral data points per image voxel. FIG. 1 illustrates an example construction of such spectral domain data. The off-resonance location of a given spin isochromat is indicated in FIG. 1. Overlapping excitation profiles that excite this isochromat are also depicted. The spectral domain, displayed in FIG. 2, is the transformation of the x-axis of FIG. 1 from isochromat off-resonance frequency to bin-excitation-frequency. Here, the bin intensity is plotted against the center excitation frequency of each bin. These bin intensities follow a Gaussian trend that ideally mimics the applied RF excitation profile.

In the methods described here, multispectral images (e.g., spectral bin images) are reconstructed from the acquired multispectral data and spectral profiles are modeled at each voxel in these images. For example, the following model can be used:

$$S_{bin}(A, v, \sigma) = Ae^{-\frac{(\delta v - v_{bin})^2}{2\sigma^2}}; \quad (4)$$

where $S_{bin}$, is the signal in the spectral bin image corresponding to the spectral bin frequency, $v_{bin}$. For each point in a spectral bin image, the spectral model can be fit to identify the parameters A, v, and σ, which are related to the amplitude, center frequency, and width of the spectral profile, respectively.

Noise in the spectral domain eliminates the viability of a simple curve-fitting approach for estimating the parameters of the spectral model. In a simple curve-fitting approach, a quadratic fit of the natural logarithm of the image signal would be performed. This approach, however, would yield wildly unstable fits on typical clinically-acquired multispectral data. Thus, rather than use a direct linear approach, an approach based on iterative perturbation theory methods is used to seek a numerically stable fit to each spectral profile in a spectral bin image.

The model outlined in Eqn. (4) can be expanded as a multi-variate Taylor series about a central point in the optimization space, $(A_0, v_0, \sigma_0)$, as follows, $$S_{bin} \approx S_{bin}(A_0, v_0, \sigma_0) + \left.\frac{\partial S_{bin}}{\partial A}\right|_{A_0, v_0, \sigma_0} \Delta A + \left.\frac{\partial S_{bin}}{\partial v}\right|_{A_0, v_0, \sigma_0} \quad (5)$$

$$\Delta v + \left.\frac{\partial S_{bin}}{\partial \sigma}\right|_{A_0,v_0,\sigma_0} \Delta \sigma;$$

where $(\Delta A, \Delta v, \Delta \sigma)$ are small perturbations from the expansion point, $(A_0, v_0, \sigma_0)$. The derivative terms are given by, $$\frac{\partial S_{bin}}{\partial A} = e^{-\frac{(v-v_{bin})^2}{2\sigma^2}} \quad (6)$$

$$\frac{\partial S_{bin}}{\partial v} = -\frac{A}{\sigma^2}(v-v_{bin})e^{-\frac{(v-v_{bin})^2}{2\sigma^2}}$$

$$\frac{\partial S_{bin}}{\partial \sigma} = \frac{A}{\sigma^3}(v-v_{bin})^2 e^{-\frac{(v-v_{bin})^2}{2\sigma^2}}.$$

Given a set of measured spectral samples, $S_{bin}^{M}$, Eqn. (5) can be used to construct a linear optimization problem, $$S_{bin}^M - S_{bin}(A_0, v_0, \sigma_0) = \left.\frac{\partial S_{bin}}{\partial A}\right|_{A_0,v_0,\sigma_0} \Delta A + \left.\frac{\partial S_{bin}}{\partial v}\right|_{A_0,v_0,\sigma_0} \quad (7)$$

$$\Delta v + \left.\frac{\partial S_{bin}}{\partial \sigma}\right|_{A_0,v_0,\sigma_0} \Delta \sigma.$$

Given a current optimization pivot point, $\vec{p}_0 = (A_0, v_0, \sigma_0)$, for a spectral profile that includes n spectral bins, this relation can be expressed in matrix form as, $$\begin{pmatrix} S_1^M - S_1(\vec{p}_0) \\ S_2^M - S_2(\vec{p}_0) \\ S_3^M - S_3(\vec{p}_0) \\ \vdots \\ S_n^M - S_n(\vec{p}_0) \end{pmatrix} = \begin{pmatrix} \left.\frac{\partial S_1}{\partial A}\right|_{\vec{p}_0} & \left.\frac{\partial S_1}{\partial v}\right|_{\vec{p}_0} & \left.\frac{\partial S_1}{\partial \sigma}\right|_{\vec{p}_0} \\ \left.\frac{\partial S_2}{\partial A}\right|_{\vec{p}_0} & \left.\frac{\partial S_2}{\partial v}\right|_{\vec{p}_0} & \left.\frac{\partial S_2}{\partial \sigma}\right|_{\vec{p}_0} \\ \left.\frac{\partial S_3}{\partial A}\right|_{\vec{p}_0} & \left.\frac{\partial S_3}{\partial v}\right|_{\vec{p}_0} & \left.\frac{\partial S_3}{\partial \sigma}\right|_{\vec{p}_0} \\ \vdots & \vdots & \vdots \\ \left.\frac{\partial S_n}{\partial A}\right|_{\vec{p}_0} & \left.\frac{\partial S_n}{\partial v}\right|_{\vec{p}_0} & \left.\frac{\partial S_n}{\partial \sigma}\right|_{\vec{p}_0} \end{pmatrix} \begin{pmatrix} \Delta A \\ \Delta v \\ \Delta \sigma \end{pmatrix}. \quad (8)$$

Through solutions of this linear system, an iterative scheme can be used to find the desired parameters, A, v, and σ. In practice, good initial estimates are utilized to build the initial optimization pivot point, $\vec{p}_0$. For example, the estimate for the amplitude parameter, A, can be taken from the maximum value of the input measured spectral profile, $S_{bin}^M$; the initial value for the center frequency parameter, v, can be extracted from a center-of-mass field map construction, such as the center-of-mass field maps described by K. Koch, et al., in "Imaging near metal with a MAVRICSEMAC hybrid," *Magnetic Resonance in Medicine*, 2011; 65:71-82; and the initial value for the spectral width parameter, σ, can be set to the spectral RF pulse design width.

The following algorithm can then be used to parameterize the spectral profile at each voxel in a spectral bin image. First, the spectral profile is extracted from the multispectral data at a given voxel, $S_{bin}^M$. Initial estimates for the optimization pivot point, $\vec{p}_0 = p_{0,j}$, are then constructed. An iterative loop over the index, i, is then entered to perform the following steps. Equation (8) is inverted to find update values, $$\vec{\Delta}_i = (\Delta A_i, \Delta v_i, \Delta \sigma_i) = \Delta_{i,j} \quad (9).$$

A temporary updated parameter solution is then generated as, $$p_{i,j}^{t} = p_{i-1,j} + \Delta_{i,j} \quad (10).$$

The solution can be regularized by checking whether each parameter update stays within established parameter bounds. If the updated parameter solution is within bounds, then the temporary solution is stored as the solution for the current iteration, $$p_{i,j} = p_{i,j}^{t} \quad (11).$$

The iterative loop is terminated based on a solution tolerance measurement or when a fixed number of iterations have been performed. The final parameter solution is then stored after the final iteration.

It is contemplated that the solution space may contain numerous local minima. Thus, the iterative approach can be stabilized by computing a minimum Euclidean norm solution for each inversion within the iterative loop. Solutions minimizing the Euclidean norm are inherently provided when using a Moore-Penrose psuedoinverse approach, which can be computed in a number of ways. For example, a computationally simple and accurate way to compute the pseudoinverse is by using a singular value decomposition ("SVD").

Given a singular decomposition of a matrix, $$A = U\Sigma V^* \quad (12);$$

its pseudoinverse, $A^\dagger$, is given as, $$A^\dagger = V\Sigma^\dagger U^* \quad (13).$$

Because the matrix, Σ, is rectangular diagonal, its pseudoinverse, $\Sigma^\dagger$, can be computed by taking the reciprocal of each non-zero element on the diagonal, leaving the zeros values in place, and finally transposing the result. In practice, only singular values beyond a given tolerance can be taken to be nonzero. The other values and associated vectors in the U and V arrays can be replaced by zeros.

As mentioned above, the spectral profile parameters can be used to suppress signal contributions from fat spins without needing to perform additional scans or to use additional preparatory RF pulses. Other applications of the spectral profile parameters can be contemplated, including improved deblurring during the combination of spectral bin images, the removal of pile-up intensity artifacts, and facilitating accelerated MSI acquisitions.

The methods described here can also be used to produce field maps. For example, a map of the center frequency parameter, V, can be used to generate a field map. Such improved field maps can be useful in applications such as detecting metallosis, where the presence of metal can otherwise make it difficult to produce an accurate field map.

Figure 3:
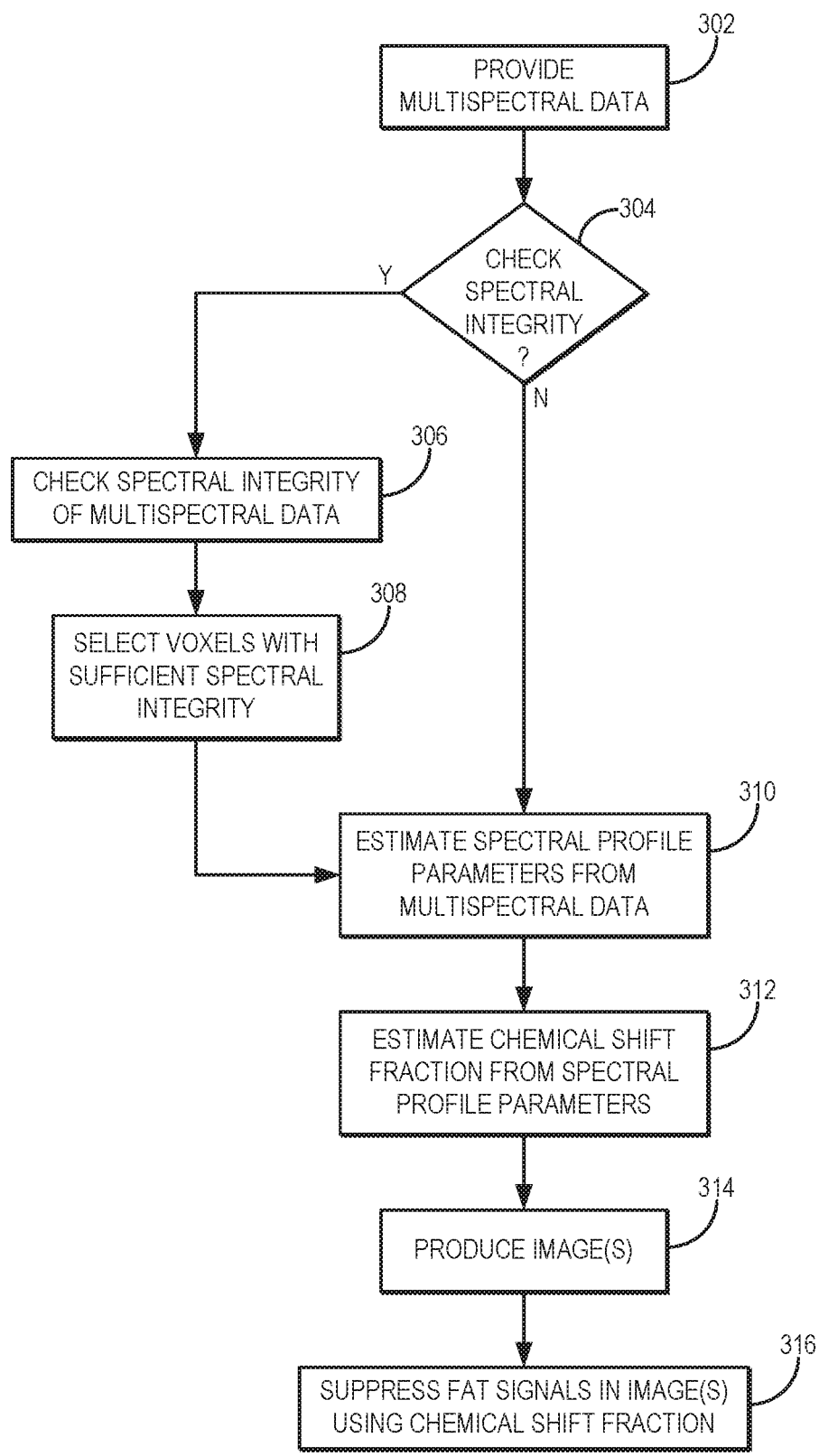
FIG. 3 is a flowchart setting forth the steps of an example method for suppressing signal contributions from fat spins in images reconstructed from multispectral data.

Referring now to FIG. 3, a flowchart is illustrated as setting forth the steps of an example method for suppressing signal contributions from fat spins in images reconstructed from multispectral data. The method includes providing multispectral data to a computer system, as indicated at step 302. As one example, the multispectral data can be provided to the computer system by retrieving previously acquired data from a data storage. As another example, the multispectral data can be provided to the computer system by acquiring the data with an MRI system that then communicated the data to the computer system, which may form a part of the MRI system. The multispectral data may include k-space data acquired using an MSI technique, or may include images reconstructed from such k-space data. When the provided data is k-space data, the spectral bin images can be reconstructed by the computer system as part of step 302.

Figure 4A:
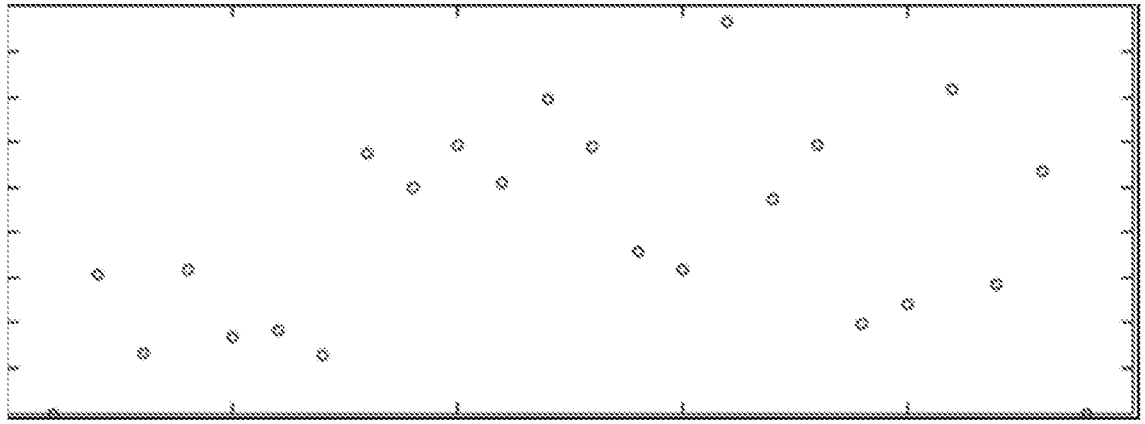
FIG. 4A is an example of spectral profile sample points in a voxel of a spectral bin image that has low spectral integrity (e.g., high noise).
Figure 4B:
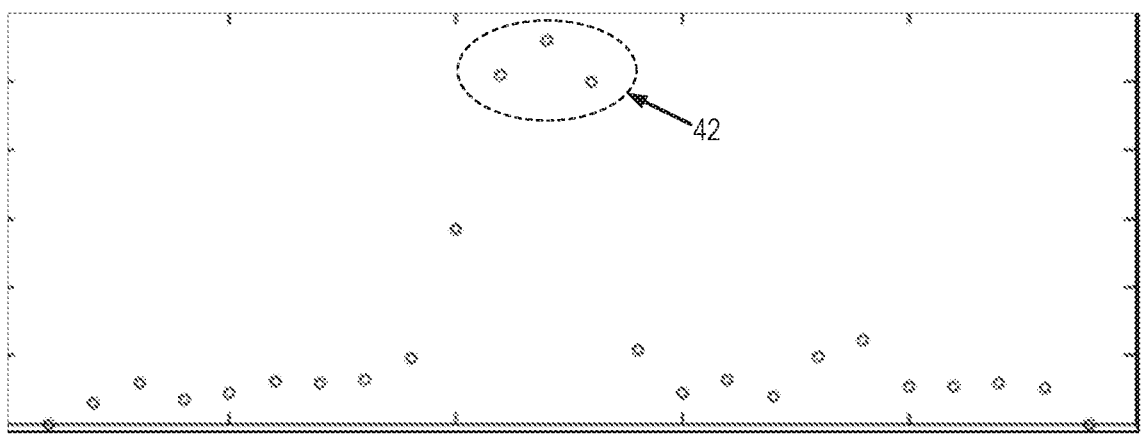
FIG. 4B is an example of spectral profile sample points in a voxel of a spectral bin image that has sufficient spectral integrity to identify a spectral profile.

A decision is made at decision block 304 whether the spectral integrity of the multispectral data should be checked. If so, then the spectral integrity is checked as indicated at step 306. FIGS. 4A and 4B show examples of data points extracted from voxels in multispectral data. FIG. 4A shows a set of data points containing significant noise. The integrity of the spectral profile sampling in that voxel is very low. In FIG. 4B, a more defined spectral profile sampling can be seen. The spectral integrity of the multispectral data can be automatically checked by processing the data to identify voxels with a well-defined spectral profile sampling (e.g., by identifying well-defined peak points, such as the points 42 in FIG. 4B). Only the voxels that are deemed to have sufficient spectral integrity are selected for processing, as indicated at step 308.

Referring again to FIG. 3, the method proceeds with estimating spectral profile parameters from the multispectral data, as indicated at step 310. The spectral profile parameters are estimated for each voxel in the multispectral data that has been selected for processing. In some examples, only the voxels selected as having sufficient spectral integrity are processed. In other examples, each voxel in the multispectral data is processed. The spectral profile parameters may be estimated as described above.

Figure 5:
FIG. 5 is an example spectral profile width parameter map, which depicts image contrast between fat and water.

An example of a spectral profile width, $\sigma$, parameter map is shown in FIG. 5. This parameter map contains an image contrast that is largely reflective of fat-water contrast. It is a discovery of the present invention that this spectral profile width information can be used to provide fat suppression.

Fat suppression near metal implants is a tremendous challenge and one of the remaining clinical gaps in performing reliable MRI near metal implants. Current 3D-MSI approaches use STIR relaxometry-based fat suppression approaches. These methods are very inefficient, however, and do not produce images with high spatial resolution or signal-to-noise ratio ("SNR").

As one example, a chemical shift fraction can be estimated based on the spectral profile width, $\sigma$, as indicated at step 312. Images reconstructed from the multispectral data (e.g., based on a combination of the spectral bin images), as indicated at step 314, can be processed at step 316 to suppress signal contributions from fat spins using the spectral profile parameters. In the example mentioned above, the chemical shift fraction can be estimated based on the spectral profile width, $\sigma$, and used to suppress the signal contributions from fat spins. The spectral width modulation effect can be used to create fat "masks" on the spectral bin images, and these masks can be applied to provide "virtual" fat suppression.

Figure 6:
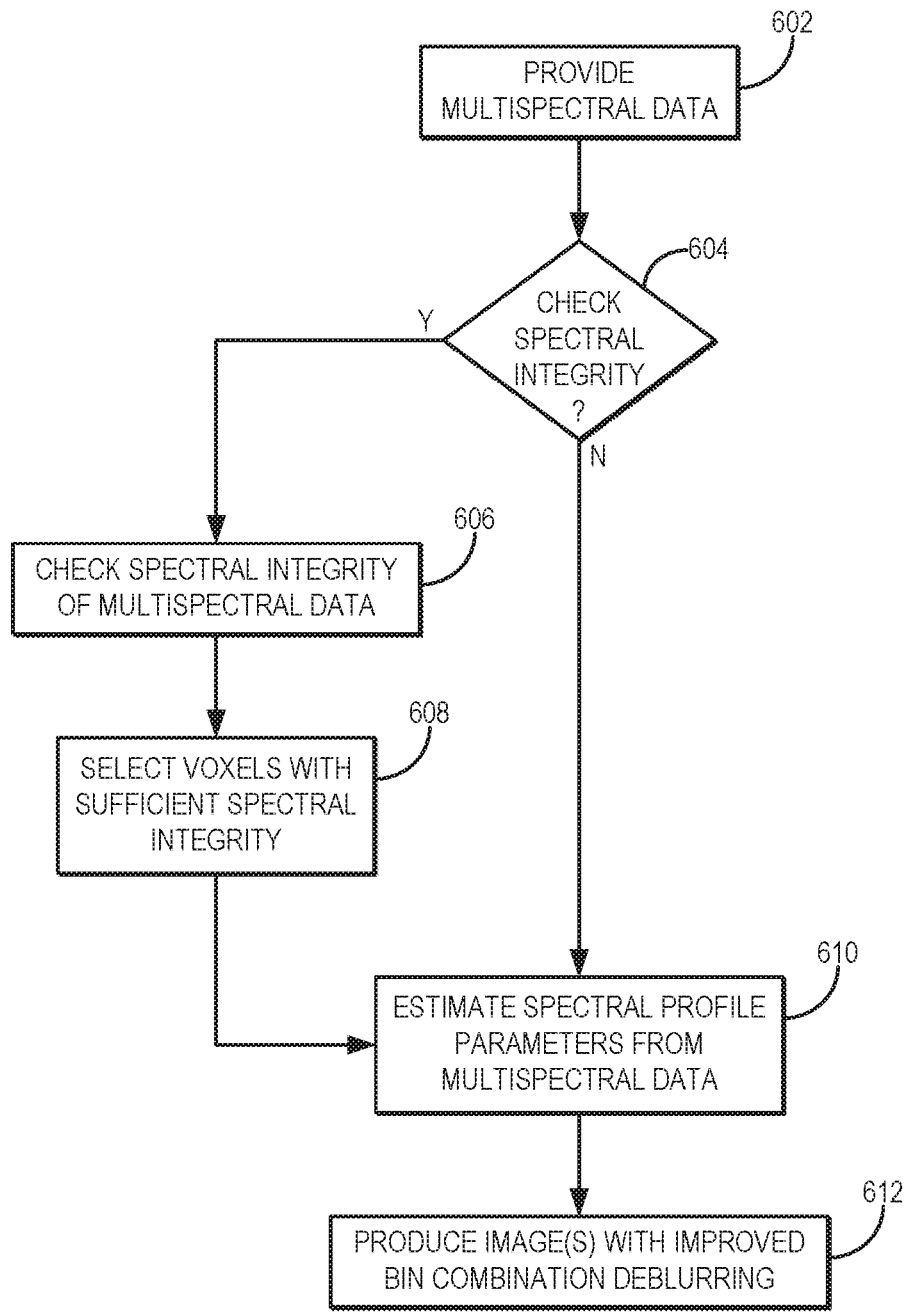
FIG. 6 is a flowchart setting forth the steps of an example method for improving deblurring when combining spectral bins during image reconstruction.

Referring now to FIG. 6, a flowchart is illustrated as setting forth the steps of an example method for improving deblurring when combining spectral bins during image reconstruction. In this method, multispectral data are provided to a computer system, as indicated at step 602. Like the method described above, a determination is made at decision block 604 whether the spectral integrity of the multispectral data should be checked. If so, the spectral integrity is checked at step 606 and the voxels with sufficient spectral integrity are selected for processing, as indicated at step 608.

Spectral profile parameters are estimated from the multispectral data, as indicated at step 610. The spectral profile parameters are estimated for each voxel in the multispectral data that has been selected for processing. In some examples, only the voxels selected as having sufficient spectral integrity are processed. In other examples, each voxel in the multispectral data is processed. The spectral profile parameters may be estimated as described above. Using the estimated spectral profile parameters, spectral bin images are then combined to form images with improved deblurring, as indicated at step 612. For example, by modeling the spectral profiles at each voxel based on the estimated spectral profile parameters, an improved deblurring can be achieved during combination of the spectral bin images. An example deblurring method that can be improved using the spectral profile parameters is described by K. Koch, et al., in "Imaging near metal with a MAVRICSEMAC hybrid," *Magnetic Resonance in Medicine,* 2011; 65:71-82.

Figure 7:
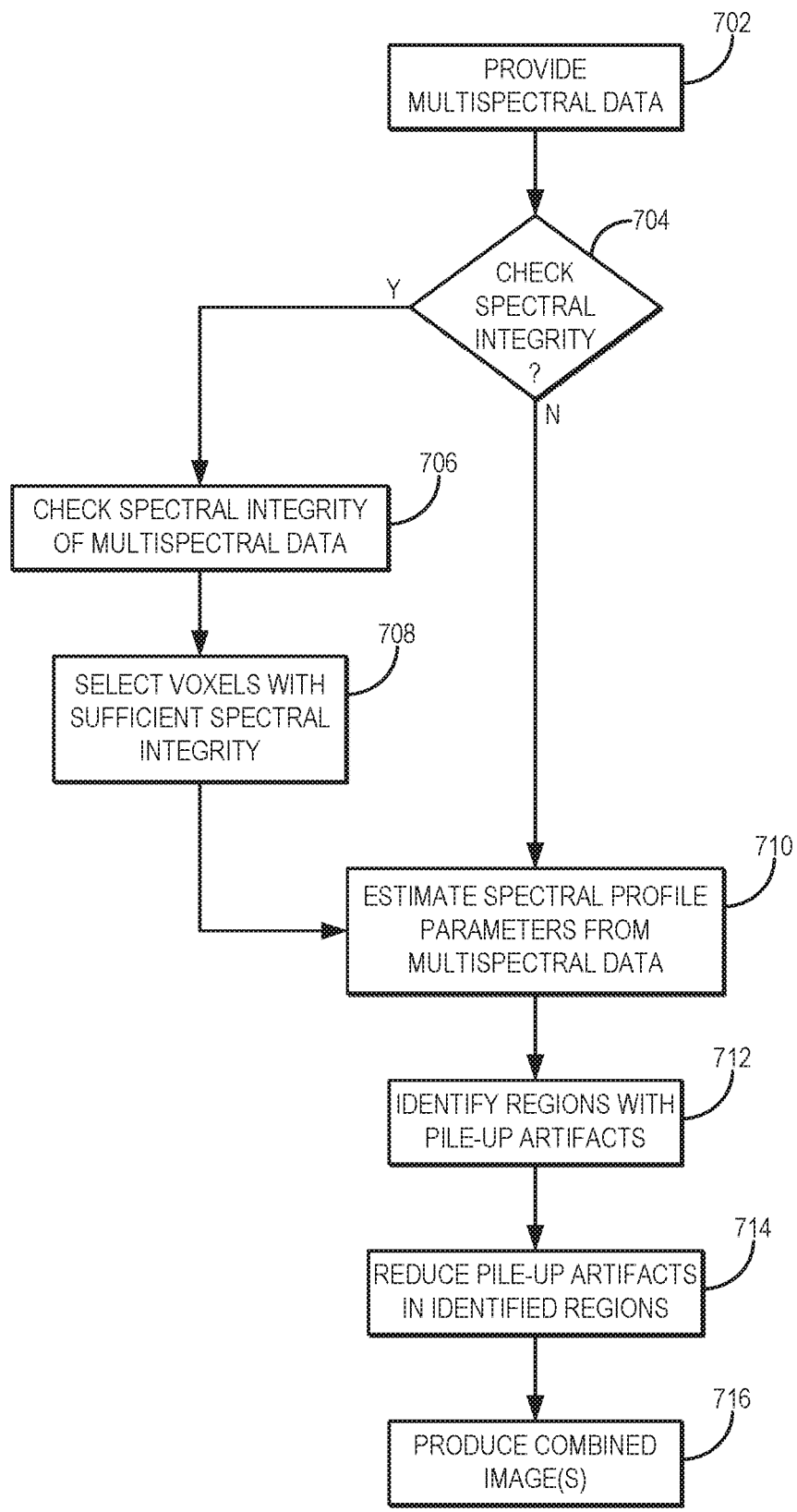
FIG. 7 is a flowchart setting forth the steps of an example method for removing or otherwise mitigating pile-up intensity artifacts.

Referring now to FIG. 7, a flowchart is illustrated as setting forth the steps of an example method for removing or otherwise mitigating pile-up intensity artifacts. In this method, multispectral data are provided to a computer system, as indicated at step 702. Like the method described above, a determination is made at decision block 704 whether the spectral integrity of the multispectral data should be checked. If so, the spectral integrity is checked at step 706 and the voxels with sufficient spectral integrity are selected for processing, as indicated at step 708.

Spectral profile parameters are estimated from the multispectral data, as indicated at step 710. The spectral profile parameters are estimated for each voxel in the multispectral data that has been selected for processing. In some examples, only the voxels selected as having sufficient spectral integrity are processed. In other examples, each voxel in the multispectral data is processed. The spectral profile parameters may be estimated as described above.

It is a discovery of the present invention that certain regions near a metallic implant show a reduction of the spectral profile width, $\sigma$. These are regions of signal "pileup" or hyperintensity artifacts that manifest in the final 3D-MSI image. This effect, known as "spectral bin compression," is a known artifactual problem in MSI techniques; however, it has been difficult to uniquely identify such regions. However, using the methods described here, regions of pile-up intensity artifacts can be identified in the spectral bin images based on an analysis of the spectral profile width, $\sigma$, as indicated at step 712. These identified regions can then be processed to remove or otherwise mitigate or suppress the pile-up intensity artifacts, as indicated at step 714. Based on the corrected spectral bin images, a final image can be produced by combining the corrected spectral bin images, as indicated at step 716.

Figure 8:
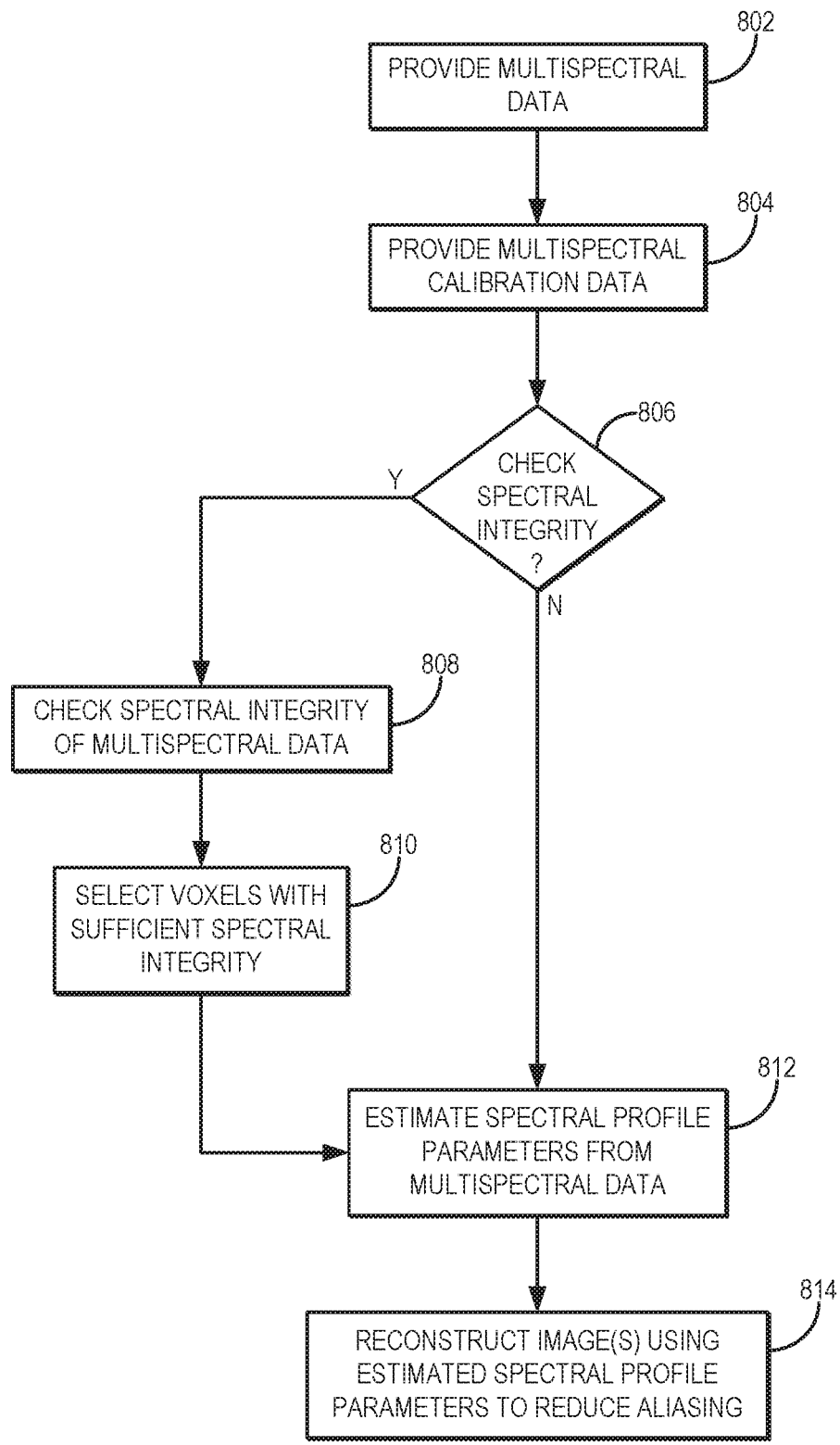
FIG. 8 is a flowchart setting forth the steps of an example method for estimating parameters of the spectral profiles and using those spectral profile parameters to accelerate an MSI data acquisition.

Referring now to FIG. 8, a flowchart is illustrated as setting forth the steps of an example method for estimating parameters of the spectral profiles and using those spectral profile parameters to accelerate an MSI data acquisition. Multispectral data are provided to a computer system processing, as indicated at step 802. These multispectral data can be provided by retrieving previously acquired data from a memory or other data storage, or by acquiring such data with an MRI system. The multispectral data generally include undersampled multispectral data that are undersampled in at least the spectral domain by acquiring fewer spectral bins in successive volumetric or slice acquisitions. In some instances, however, the multispectral data can include one or more sets of data acquired with full spectral sampling, as will be described below in more detail.

As one example, the multispectral data can be acquired using a diffusion imaging sequence. In these examples, the undersampled multispectral data can include data acquired with multiple different diffusion encodings (e.g., different b-values). In such acquisitions, the b=0 data can be acquired with full spectral sampling, whereas the b>0 data can be acquired with spectral undersampling.

As another example, multispectral data can be acquired using a dynamic imaging sequence. As one example, the dynamic imaging sequence can include a dynamic contrast enhanced ("DCE") sequence. In these examples, the multispectral data can include one acquisition of the volume with full spectral sampling and subsequent acquisitions with spectral undersampling. For instance, an image volume with full spectral sampling can be acquired before administering a contrast agent, and undersampling multispectral data can be acquired while the contrast agent is passing through the subject's vasculature. In other examples, the multispectral data can all be undersampled.

In still other examples, the multispectral data can be acquired using other imaging sequences in which the same volume, slice, or series of slices, is imaged repeatedly. Examples of such sequences include those used for magnetic resonance thermometry, relaxometry, functional MRI, or other acquisitions where multiple image volumes or slices are acquired in a relatively quick succession to capture dynamic or multi-parametric phenomena. In these examples, the multispectral data can all be undersampled, or can include one or more volumes or slices that are fully spectrally sampled.

Multispectral calibration data are then provided to the computer system, as indicated at step 804. As described above, the calibration data can be derived from, or already included in, the multispectral data (e.g., one or more slices or volumes that are fully spectrally sampled). In examples where the provided multispectral data are all spectrally undersampled, the calibration data can be acquired using the calibration scan methods described in co-pending PCT Patent Application No. WO2016/187014, which is herein incorporated by reference in its entirety. The calibration data acquired using such a calibration scan has a lower spatial resolution and thus can be acquired rapidly.

Spectral profile parameters can be estimated from the calibration data to characterize the spectral profiles at the voxels in the calibration data. Even if the calibration data have a lower spatial resolution, this spectral profile information can be used to estimate missing data from an undersampled MSI acquisition.

Thus, the method proceeds with determining at decision block 806 whether the spectral integrity of the multispectral calibration data should be checked. If so, the spectral integrity is checked at step 808 and the voxels with sufficient spectral integrity are selected for processing, as indicated at step 810.

Spectral profile parameters can be estimated from the multispectral calibration data, as indicated at step 812. In these instances, the spectral profile parameters are estimated for each voxel in the multispectral calibration data that has been selected for processing. In some examples, only the voxels selected as having sufficient spectral integrity are processed. In other examples, each voxel in the multispectral calibration data is processed.

In some embodiments, the spectral profile parameters may be estimated as described above. In other embodiments, the spectral profile parameters can include a local model of the spectrum that can be estimated by computing a cubic spline model of the spectral domain from the calibration data. Models other than a cubic spline can also be implemented, including other spline-based models and other polynomial models, whether piece-wise defined or otherwise. In still other embodiments, a dictionary matching process can be implemented to estimate the spectral profile parameters.

The spectral profile information estimated in step 812 can then be used to estimate missing data in this higher resolution multispectral data, such that aliasing artifacts are mitigated in the images reconstructed from the undersampled multispectral data, as indicated at step 814. For example, the undersampled spectral points in the multispectral data can be fit to a spectral model based at least in part on the spectral profile information to interpolate the missing spectral acquisitions. In such instances, the missing data are estimated using a local interpolation approach.

Thus, the spectral profile modeling described above can be used to undersample multi-volume MSI acquisitions. Example multi-volume MSI implementations that could benefit from such undersampling include diffusion imaging, dynamic imaging, thermometry, relaxometry, and other imaging applications where the same volume is repeatedly imaged.

As described above, in one example, multiple b-value diffusion-weighted MSI acquisitions can be performed more rapidly using the undersampling provided by the methods described above. For the purposes of undersampling multiple b-value MSI acquisitions, the fully spectrally sampled b=0 data can be used to estimate the spectral profile parameters. The amplitude adjustment of this spectral profile model can then be used to fill in the missing points for each undersampled b-value voxel.

It is contemplated that the result of this undersampling can include a two-fold net undersampling of all b>0 images in the acquisition. The same strategy could be applied to dynamic imaging, as also described above. With a dynamic 2D-MSI implementation, the method described above (with a 50 percent reduction of required bin samples in the time course) could allow for single-slice imaging near total hip replacements in 1-2 second temporal resolution. This temporal resolution opens up the possibility of dynamic contrast enhanced ("DCE") MSI directly near metal implants, which has not previously been demonstrated.

Figure 9:
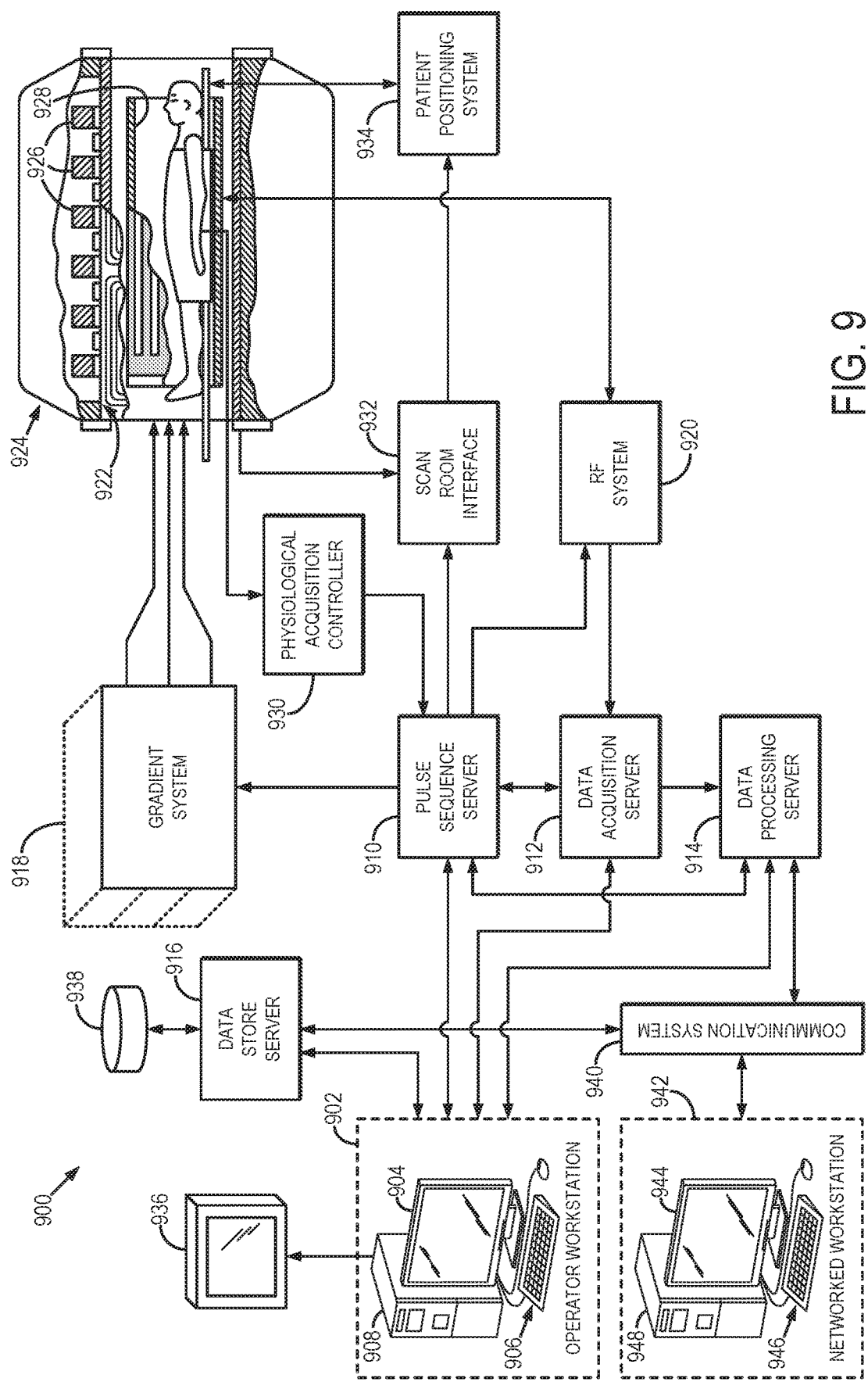
FIG. 9 is an example of a magnetic resonance imaging ("MRI") system that can implement the methods described here.

Referring particularly now to FIG. 9, an example of a magnetic resonance imaging ("MRI") system 900 that can implement the methods described here is illustrated. The MRI system 900 includes an operator workstation 902 that may include a display 904, one or more input devices 906 (e.g., a keyboard, a mouse), and a processor 908. The processor 908 may include a commercially available programmable machine running a commercially available operating system. The operator workstation 902 provides an operator interface that facilitates entering scan parameters into the MRI system 900. The operator workstation 902 may be coupled to different servers, including, for example, a pulse sequence server 910, a data acquisition server 912, a data processing server 914, and a data store server 916. The operator workstation 902 and the servers 910, 912, 914, and 916 may be connected via a communication system 940, which may include wired or wireless network connections.

The pulse sequence server 910 functions in response to instructions provided by the operator workstation 902 to operate a gradient system 918 and a radiofrequency ("RF") system 920. Gradient waveforms for performing a prescribed scan are produced and applied to the gradient system 918, which then excites gradient coils in a gradient coil assembly 922 to produce the magnetic field gradients $G_x$, $G_y$, and $G_z$ that are used for spatially encoding magnetic resonance signals. The gradient coil assembly 922 forms part of a magnet assembly 924 that includes a polarizing magnet 926 and a whole-body RF coil 928.

RF waveforms are applied by the RF system 920 to the RF coil 928, or a separate local coil to perform the prescribed magnetic resonance pulse sequence. Responsive magnetic resonance signals detected by the RF coil 928, or a separate local coil, are received by the RF system 920. The responsive magnetic resonance signals may be amplified, demodulated, filtered, and digitized under direction of commands produced by the pulse sequence server 910. The RF system 920 includes an RF transmitter for producing a wide variety of RF pulses used in MRI pulse sequences. The RF transmitter is responsive to the prescribed scan and direction from the pulse sequence server 910 to produce RF pulses of the desired frequency, phase, and pulse amplitude waveform. The generated RF pulses may be applied to the whole-body RF coil 928 or to one or more local coils or coil arrays.

The RF system 920 also includes one or more RF receiver channels. An RF receiver channel includes an RF preamplifier that amplifies the magnetic resonance signal received by the coil 928 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \qquad (14);$$

and the phase of the received magnetic resonance signal may also be determined according to the following relationship:

$$\varphi = \tan^{-1}\left(\frac{Q}{I}\right). \qquad (15)$$

The pulse sequence server 910 may receive patient data from a physiological acquisition controller 930. By way of example, the physiological acquisition controller 930 may receive signals from a number of different sensors connected to the patient, including electrocardiograph ("ECG") signals from electrodes, or respiratory signals from a respiratory bellows or other respiratory monitoring devices. These signals may be used by the pulse sequence server 910 to synchronize, or "gate," the performance of the scan with the subject's heart beat or respiration.

The pulse sequence server 910 may also connect to a scan room interface circuit 932 that receives signals from various sensors associated with the condition of the patient and the magnet system. Through the scan room interface circuit 932, a patient positioning system 934 can receive commands to move the patient to desired positions during the scan.

The digitized magnetic resonance signal samples produced by the RF system 920 are received by the data acquisition server 912. The data acquisition server 912 operates in response to instructions downloaded from the operator workstation 902 to receive the real-time magnetic resonance data and provide buffer storage, so that data is not lost by data overrun. In some scans, the data acquisition server 912 passes the acquired magnetic resonance data to the data processing server 914. In scans that require information derived from acquired magnetic resonance data to control the further performance of the scan, the data acquisition server 912 may be programmed to produce such information and convey it to the pulse sequence server 910.

For example, during pre-scans, magnetic resonance data may be acquired and used to calibrate the pulse sequence performed by the pulse sequence server 910. As another example, navigator signals may be acquired and used to adjust the operating parameters of the RF system 920 or the gradient system 918, or to control the view order in which k-space is sampled. In still another example, the data acquisition server 912 may also process magnetic resonance signals used to detect the arrival of a contrast agent in a magnetic resonance angiography ("MRA") scan. For example, the data acquisition server 912 may acquire magnetic resonance data and processes it in real-time to produce information that is used to control the scan.

The data processing server 914 receives magnetic resonance data from the data acquisition server 912 and processes the magnetic resonance data in accordance with instructions provided by the operator workstation 902. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 914 are conveyed back to the operator workstation 902 for storage. Real-time images may be stored in a data base memory cache, from which they may be output to operator display 902 or a display 936. Batch mode images or selected real time images may be stored in a host database on disc storage 938. When such images have been reconstructed and transferred to storage, the data processing server 914 may notify the data store server 916 on the operator workstation 902. The operator workstation 902 may be used by an operator to archive the images, produce films, or send the images via a network to other facilities.

The MRI system 900 may also include one or more networked workstations 942. For example, a networked workstation 942 may include a display 944, one or more input devices 946 (e.g., a keyboard, a mouse), and a processor 948. The networked workstation 942 may be located within the same facility as the operator workstation 902, or in a different facility, such as a different healthcare institution or clinic.

The networked workstation 942 may gain remote access to the data processing server 914 or data store server 916 via the communication system 940. Accordingly, multiple networked workstations 942 may have access to the data processing server 914 and the data store server 916. In this manner, magnetic resonance data, reconstructed images, or other data may be exchanged between the data processing server 914 or the data store server 916 and the networked workstations 942, such that the data or images may be remotely processed by a networked workstation 942.

The present disclosure has described one or more preferred embodiments, and it should be appreciated that many equivalents, alternatives, variations, and modifications, aside from those expressly stated, are possible and within the scope of the invention.

The invention claimed is:

1. A method for multispectral magnetic resonance imaging (MRI), the steps of the method comprising:
    (a) providing to a computer system, multispectral data acquired from a subject with an MRI system, wherein the multispectral data contain at least some multispectral data that are undersampled in a spectral domain by acquiring multispectral data from fewer spectral bins relative to fully spectrally sampled multispectral data;
(b) providing to the computer system, multispectral calibration data;
(c) generating a spectral model based at least in part on the multispectral calibration data;
(d) estimating missing multispectral data for spectral bins not sampled in the provided multispectral data using the spectral model; and
(e) reconstructing an image of the subject from the provided multispectral data and the estimated missing multispectral data.

2. The method as recited in claim 1, wherein generating the spectral model includes computing a polynomial-based model from the multispectral calibration data.

3. The method as recited in claim 2, wherein the polynomial-based model is a spline-based model.

4. The method as recited in claim 3, wherein the spline-based model is a cubic spline model.

5. The method as recited in claim 2, wherein estimating the missing multispectral data includes interpolating the missing multispectral data using the spectral model.

6. The method as recited in claim 1, wherein estimating the missing multispectral data includes interpolating the missing multispectral data using the spectral model.

7. The method as recited in claim 1, wherein providing the multispectral calibration data includes deriving the multispectral calibration data from the provided multispectral data.

8. The method as recited in claim 7, wherein the multispectral data comprises diffusion-weighted multispectral data that are undersampled in the spectral domain and multispectral data acquired with a zero b-value and that are fully sampled in the spectral domain, wherein the multispectral calibration data are provided as the multispectral data acquired with the zero b-value.

9. The method as recited in claim 7, wherein the multispectral data comprises dynamic contrast enhanced multispectral data that are undersampled in the spectral domain and at least one multispectral data set acquired that fully samples the spectral domain, wherein the multispectral calibration data are provided as the at least one multispectral data set acquired that fully samples the spectral domain.

10. The method as recited in claim 7, wherein the multispectral data comprises multispectral data acquired from one of a volume or a slice over a plurality of different time frames such that multispectral data acquired at one of the plurality of different time frames is fully sampled multispectral data, and wherein the multispectral calibration data are provided as the multispectral data acquired at the one of the plurality of different time frames that is fully sampled multispectral data.

11. A method for accelerating a multispectral magnetic resonance imaging (MRI) data acquisition, the steps of the method comprising:
(a) providing to a computer system, multispectral calibration data acquired from a subject with an MRI system;
(b) estimating spectral profile parameters at each voxel in the multispectral calibration data, wherein the spectral profile parameters are based on modeling signals at each voxel using a spectral profile model;
(c) acquiring undersampled multispectral data from the subject with the MRI system using a multispectral imaging (MSI) acquisition by acquiring multispectral data from fewer spectral bins relative to fully spectrally sampled multispectral data;
(d) estimating missing multispectral data for spectral bins not sampled in the acquired multispectral data using the estimated spectral profile parameters; and
(e) reconstructing an image of the subject from the undersampled multispectral data and the estimated missing multispectral data.

12. A method for suppressing fat signals in multispectral magnetic resonance images, the steps of the method comprising:
(a) providing to a computer system, multispectral data acquired from a subject with an MRI system using a multispectral imaging (MSI) acquisition;
(b) estimating spectral profile parameters at each voxel in the multispectral data, wherein the spectral profile parameters are based on modeling signals at each voxel using a spectral profile model and include at least a width of the spectral profile;
(c) estimating a chemical shift fraction associated with signal contributions from fat spins using the estimated width of the spectral profile;
(d) reconstructing an image of the subject from the multispectral data; and
(e) suppressing signal contributions from fat spins in the reconstructed image using the estimated chemical shift fraction.

13. The method as recited in claim 12, wherein step (b) includes selecting voxels in the multispectral data that have sufficient spectral integrity to identify spectral profiles therein, and estimating the spectral profile parameters only at the selected voxels.

14. The method as recited in claim 13, wherein selecting the voxels that have sufficient spectral integrity includes identifying voxels with spectral profile sample points that are associated with a spectral profile peak.

15. The method as recited in claim 12, wherein step (b) includes estimating the spectral parameters based on iterative perturbations of the spectral parameters from an initial pivot point defined by initial values of the spectral parameters.

16. The method as recited in claim 15, wherein the spectral parameters include a spectral profile amplitude, a spectral profile center frequency, and the width of the spectral profile.

17. The method as recited in claim 16, wherein an initial value of the spectral profile amplitude is selected as a maximum value of spectral profile samples at the voxel being processed; an initial value of the spectral profile center frequency is determined from a field map computed from the multispectral data; and an initial value of the width of the spectral profile is selected as a width of a spectral radio frequency (RF) pulse used to acquire the multispectral data.

18. A method for identifying regions of signal pile-up artifacts from multispectral magnetic resonance images, the steps of the method comprising:
(a) providing to a computer system, multispectral data acquired from a subject with an MRI system using a multispectral imaging (MSI) acquisition;
(b) estimating spectral profile parameters at each voxel in the multispectral data, wherein the spectral profile parameters are based on modeling signals at each voxel using a spectral profile model and include at least a width of the spectral profile; and
(c) identifying voxels associated with pile-up intensity artifacts based on the width of the spectral profile estimated for each voxel.

19. The method as recited in claim 18, further comprising:
(d) processing the identified voxels in the multispectral data to remove the pile-up intensity artifacts; and
(e) reconstructing an image of the subject from the processed multispectral data, wherein pile-up intensity artifacts in the reconstructed image are mitigated.

* * * * *